US008912381B2

(12) United States Patent
Chinta et al.

(10) Patent No.: US 8,912,381 B2
(45) Date of Patent: Dec. 16, 2014

(54) PROCESS FOR THE OXIDATIVE COUPLING OF METHANE

(75) Inventors: Sivadinarayana Chinta, Missouri City, TX (US); Joseph Thorman, Houston, TX (US); James Butler, League City, TX (US); Joe Hunter, Friendswood, TX (US); Taylor Rives, Houston, TX (US)

(73) Assignee: Fina Technology, Inc., Houston, TX (US)

( * ) Notice: Subject to any disclaimer, the term of this patent is extended or adjusted under 35 U.S.C. 154(b) by 471 days.

(21) Appl. No.: 12/494,117

(22) Filed: Jun. 29, 2009

(65) Prior Publication Data

US 2010/0331595 A1 Dec. 30, 2010

(51) Int. Cl.
 *C07C 2/84* (2006.01)
 *B01J 23/10* (2006.01)
 *B01J 23/36* (2006.01)
 *B01J 23/02* (2006.01)
 *B01J 21/10* (2006.01)

(52) U.S. Cl.
 CPC ............... *C07C 2/84* (2013.01); *C07C 2523/36* (2013.01); *B01J 23/02* (2013.01); *C07C 2521/10* (2013.01); *C07C 2523/02* (2013.01); *B01J 23/10* (2013.01); *B01J 23/36* (2013.01); *C07C 2523/10* (2013.01); *B01J 21/10* (2013.01); *Y10S 585/906* (2013.01)
 USPC ............ 585/658; 585/654; 585/656; 585/906

(58) Field of Classification Search
 USPC .................. 585/500, 654, 656, 658, 700, 906
 See application file for complete search history.

(56) References Cited

U.S. PATENT DOCUMENTS

| | | | |
|---|---|---|---|
| 4,239,658 A | 12/1980 | Mitchell, III et al. | |
| 4,523,049 A | 6/1985 | Jones et al. | |
| 4,547,610 A | 10/1985 | Sofranko et al. | |
| 4,547,611 A * | 10/1985 | Jones et al. | 585/500 |
| 4,656,144 A | 4/1987 | Hosaka et al. | |
| 4,658,076 A | 4/1987 | Kolts et al. | |
| 4,658,077 A | 4/1987 | Kolts et al. | |
| 4,672,145 A | 6/1987 | Kolts et al. | |
| 4,704,487 A | 11/1987 | Devries et al. | |
| 4,704,493 A | 11/1987 | Devries et al. | |
| 4,774,216 A | 9/1988 | Kolts et al. | |
| 4,775,654 A | 10/1988 | Kolts et al. | |
| 4,780,449 A * | 10/1988 | Hicks | 502/303 |
| 4,822,944 A * | 4/1989 | Brazdil et al. | 585/500 |
| 4,826,796 A | 5/1989 | Erekson et al. | |
| 4,886,931 A * | 12/1989 | Bartek et al. | 585/500 |
| 4,895,823 A | 1/1990 | Kolts et al. | |
| 4,935,572 A * | 6/1990 | Erekson et al. | 585/415 |
| 4,950,827 A | 8/1990 | Erekson et al. | |
| 4,950,830 A | 8/1990 | Erekson et al. | |
| 4,950,836 A | 8/1990 | Kimble et al. | |
| 4,956,327 A | 9/1990 | Erekson et al. | |
| 4,962,252 A | 10/1990 | Wade | |
| 4,982,038 A | 1/1991 | Kimble et al. | |
| 5,028,577 A | 7/1991 | Michaels et al. | |
| 5,068,215 A | 11/1991 | Bartek et al. | |
| 5,087,787 A | 2/1992 | Kimble et al. | |
| 5,097,086 A | 3/1992 | Lee et al. | |
| 5,105,045 A | 4/1992 | Kimble et al. | |
| 5,118,654 A * | 6/1992 | Choudhary et al. | 502/340 |
| 5,118,899 A * | 6/1992 | Kimble et al. | 585/500 |
| 5,132,482 A | 7/1992 | Smith et al. | |
| 5,146,027 A | 9/1992 | Gaffney | |
| 5,157,188 A | 10/1992 | Kolts et al. | |
| 5,160,502 A | 11/1992 | Kimble et al. | |
| 5,210,357 A | 5/1993 | Kolts et al. | |
| 5,238,898 A | 8/1993 | Han et al. | |
| 5,321,188 A * | 6/1994 | Fornasari et al. | 585/500 |
| 5,406,017 A | 4/1995 | Withers, Jr. | |
| 5,527,978 A * | 6/1996 | Fornasari et al. | 585/500 |
| 5,763,722 A * | 6/1998 | Vic et al. | 585/500 |
| 5,959,170 A | 9/1999 | Withers, Jr. | |
| 6,020,533 A | 2/2000 | Lewis et al. | |
| 6,087,545 A * | 7/2000 | Choudhary et al. | 585/658 |
| 6,096,934 A | 8/2000 | Rekoske | |
| 2002/0173420 A1 | 11/2002 | Cantrell et al. | |
| 2007/0055083 A1 | 3/2007 | Bagherzadeh et al. | |
| 2008/0281136 A1 | 11/2008 | Bagherzadeh et al. | |

FOREIGN PATENT DOCUMENTS

| | | |
|---|---|---|
| CA | 2016675 A1 | 11/1991 |
| WO | 2011/133643 A1 | 10/2011 |

OTHER PUBLICATIONS

Tung, et al., "Oxidative Coupling of Methane over Li/MgO: Kinetics and Mechanisms" in Ind. Eng. Chem. Res., 1992, 31, 1621-1625—1992, month unknown.*
Haber, Block and Delmon. "Manual of Methods and Procedures for Catalyst Characterization", Pure & Appl. Chem., vol. 67, Nos. 8/9, pp. 1257-1306 (1995).

(Continued)

*Primary Examiner* — In Suk Bullock
*Assistant Examiner* — Bradley Etherton

(57) ABSTRACT

A method for the oxidative coupling of hydrocarbons, such as the oxidative coupling of methane, includes providing an oxidative catalyst inside a reactor, and carrying out the oxidative coupling reaction under a set of reaction conditions. The oxidative catalyst includes (A) at least one element selected from the group consisting of the Lanthanoid group, Mg, Ca, and the elements of Group 4 of the periodic table (Ti, Zr, and Hf); (B) at least one element selected from the group consisting of the Group 1 elements of Li, Na, K, Rb, Cs, and the elements of Group 3 (including La and Ac) and Groups 5-15 of the periodic table; (C) at least one element selected from the group consisting of the Group 1 elements of Li, Na, K, Rb, Cs, and the elements Ca, Sr, and Ba; and (D) oxygen.

23 Claims, 1 Drawing Sheet

(56) References Cited

OTHER PUBLICATIONS

Khan and Ruckenstein. "Oxidative Methylation of Toluene with Methane over Superbasic Catalysts: A Selective Route to Styrene and Ethylbenzene through Alternative Feedstocks", Journal of Catalysis 143, pp. 1-21 (1993).
Lunsford, J.H. "The Catalytic Oxidative Coupling of Methane", Angew, Chem. Intl. Ed. Engl. 34, p. 970 (1995).
Extended European Search Report issued in European Application No. 10800251.0-1454 dated Oct. 28, 2013 (10 pages).
Bi Yingli et al: "Catalytic Oxidative Coupling of Methane over Alkali, Alkaline Earth and Rare Earth Metal Oxides", Applied Catalysis, May 16, 1988, pp. 185-190, XP055084140.
Office Action issued in Japanese Application No. 2012-517752 dated Jun. 4, 2014, and English translation thereof (9 pages).

* cited by examiner

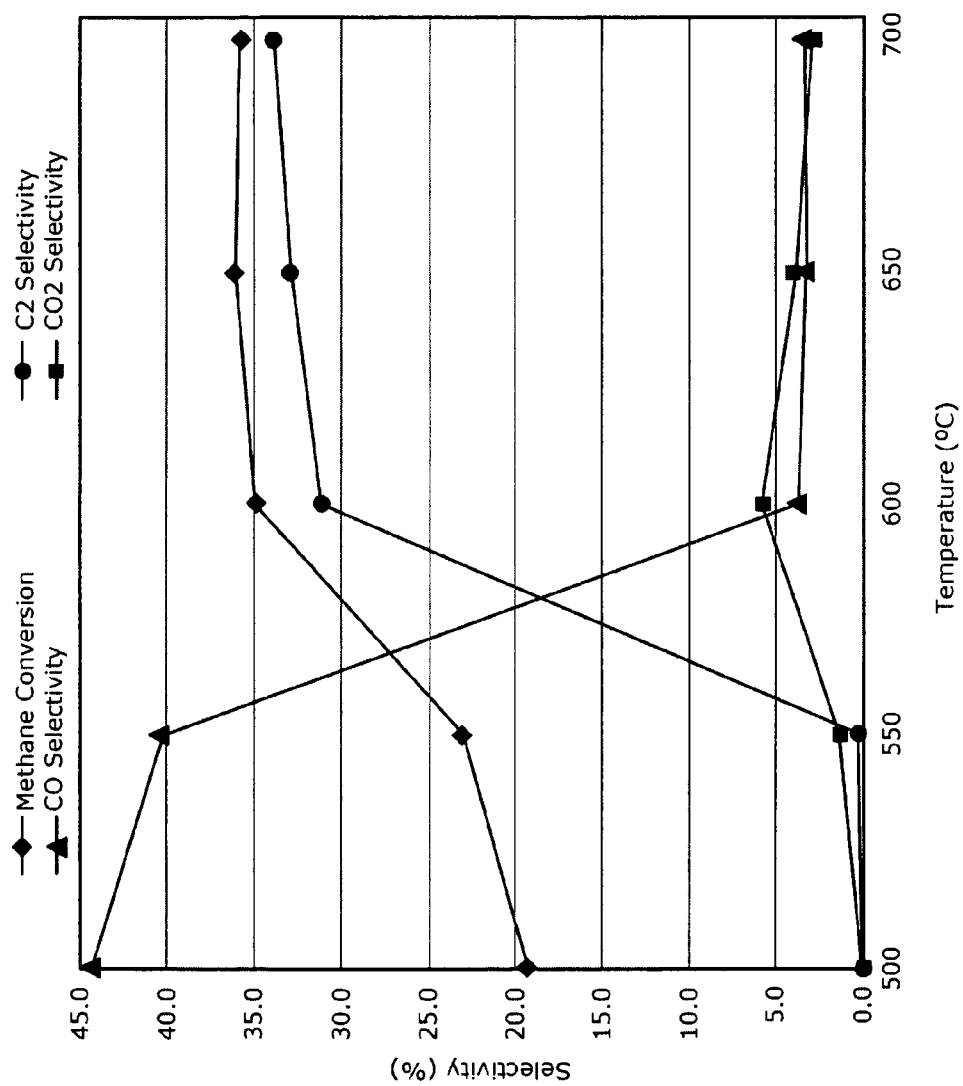

PROCESS FOR THE OXIDATIVE COUPLING OF METHANE

CROSS-REFERENCE TO RELATED APPLICATIONS

The present invention is related to co-pending applications titled: Catalysts For Oxidative Coupling of Hydrocarbons; and Process For The Oxidative Coupling of Hydrocarbons, both filed by Fina Technology, Inc. on the same date as the present application.

FIELD

The present invention generally relates to the oxidative coupling of methane.

BACKGROUND

Methane is a primary component of natural gas. Although natural gas can be useful as a fuel, natural gas sources can be remote, and often, it is not cost effective to transport the methane. One method of transporting natural gas is by liquefying the gas, however, the boiling point of methane is low enough that liquefaction can be difficult and expensive. Research has been conducted to find new and cost-effective ways of utilizing this resource.

One possible solution is to convert methane to higher hydrocarbons such as ethane or ethylene. Ethylene and higher hydrocarbons can be more easily liquefied and transported from remote sites and can also be valuable products. Ethylene, for one, can be a valuable product, as it can be used for the production of styrene, and has many other uses, such as the production of polyethylene, ethanol, ethylene glycol, and polyvinyl chloride.

Traditionally, ethylene is obtained predominantly from the thermal cracking of hydrocarbons, such as ethane, propane, butane, or naphtha. Ethylene can also be produced and recovered from various refinery processes. Ethylene from these sources can also include a variety of undesired products, including diolefins and acetylene, which can be costly to separate from the ethylene. Separation methods can include, for example, extractive distillation and selective hydrogenation of the acetylene back to ethylene. Thermal cracking and separation technologies for the production of relatively pure ethylene can result in significant production costs. Thus, the production of ethylene from methane rather than by some of the traditional routes could decrease ethylene production costs.

SUMMARY

Embodiments of the present invention generally include a method for the oxidative coupling of hydrocarbons, such as the oxidative coupling of methane. The method can include the steps of preparing oxidative catalysts and running the oxidative coupling reaction inside the reactor over the oxidative catalyst, according to a set of reaction conditions.

An embodiment of the present invention is the preparation and/or use of a catalyst that includes (A) at least one element selected from the group consisting of the Lanthanoid group, Mg, Ca, and the elements of Group 4 of the periodic table (Ti, Zr, and Hf). The catalyst further includes (B) at least one element selected from the group consisting of the Group 1 elements of Li, Na, K, Rb, Cs, and the elements of Group 3 (including La and Ac) and Groups 5-15 of the periodic table and (C) at least one element selected from the group consisting of the Group 1 elements of Li, Na, K, Rb, Cs, and the elements Ca, Sr, and Ba; along with (D) oxygen. If an element from Group 1 of the periodic table is used in (B), it cannot be used in (C). The catalyst can then be dried, calcined, and meshed before being placed in a reactor. The catalyst can be calcined by heating the catalyst to elevated temperatures, such as above 750° C.

The element(s) selected from (A) can range from 40 to 90 wt % of the catalyst. The element(s) selected from (B) can range from 0.01 to 40 wt % of the catalyst. The element(s) selected from (C) can range from 0.01 to 40 wt % of the catalyst. The oxygen in (D) can range from 10 to 45 wt % of the catalyst.

The oxidative coupling reaction includes supplying the hydrocarbons, such as methane, along with an oxygen source to the reactor. The catalyst can be used in a reactor for the oxidative coupling of methane (OCM). For OCM, the temperature can be from 500° C. to 750° C., optionally from 600° C. to 750° C. The molar ratio of methane to oxygen can be from 1:1 to 100:1, optionally from 4:1 to 80:1.

The product distribution of the oxidative coupling reaction can be altered by adjusting the temperature of the reactor. Adjusting the temperature can also alter the exotherm produced by oxidative coupling.

An embodiment of the invention is a method for the oxidative coupling of methane that includes providing a hydrocarbon feedstream including methane and providing an oxidative catalyst within a reactor. The catalyst includes (A) at least one element selected from the group consisting of the Lanthanoid group, Mg, Ca, and the elements of Group 4 of the periodic table (Ti, Zr, and Hf) the elements from (A) ranging from 40 to 90 wt % of the catalyst; (B) at least one element selected from the group consisting of the Group 1 elements of Li, Na, K, Rb, Cs, and the elements of Group 3 (including La and Ac) and Groups 5-15 of the periodic table, the elements from (B) ranging from 0.01 to 40 wt % of the catalyst; (C) at least one element selected from the group consisting of the Group 1 elements of Li, Na, K, Rb, Cs, and the elements Ca, Sr, and Ba, the elements from (C) ranging from 0.01 to 40 wt % of the catalyst; and (D) oxygen ranging from 10 to 45 wt % of the catalyst; wherein if an element from Group 1 of the periodic table is used in (B), it cannot be used in (C); wherein the catalyst is calcined after the elements are combined. The hydrocarbon feedstream and an oxygen source are fed to the reactor wherein oxidative coupling of methane to methane occurs over the oxidative catalyst according to a set of reactions conditions. A product stream that includes ethane and ethylene is recovered from the reactor.

The reactor temperature can range from 500° C. to 750° C. and the molar ratio of methane to oxygen can range from 1:1 to 100:1. Alternately the temperature can range from 600° C. to 750° C. and the molar ratio of methane to oxygen from 4:1 to 80:1. The catalyst can be pretreated in the reactor before it is used for the oxidative coupling of hydrocarbons, the pretreatment consisting of heating the catalyst to above 750° C.

The composition of the product hydrocarbons can be adjusted by adjusting the temperature of the reaction. The composition can also be adjusted by adjusting the space velocity of the reaction.

BRIEF DESCRIPTION OF DRAWINGS

FIG. 1 is a graph displaying data, including methane conversion and selectivity of product hydrocarbons, of the OCM trials from Example B.

DETAILED DESCRIPTION

The results of oxidative coupling reactions can be influenced by many factors, such as reaction conditions, source and contents of the feed, and reactor design. The catalyst used for the reaction can be one of the most important factors. The effectiveness of the reaction can be measured in terms of conversion, selectivity, and yield. Conversion refers to the percentage of reactant (e.g. methane) that undergoes a chemical reaction. Selectivity refers to the relative activity of a catalyst in reference to a particular compound in a mixture. Selectivity is quantified as the proportion of a particular product relative to all others.

An embodiment of the present invention is a process of OCM. The process can include steps such as preparing an oxidative catalyst, pretreating the oxidative catalyst inside a reactor, and carrying out the oxidative coupling reaction inside the reactor, according to a set of reaction conditions. Preparation and pretreatment of the catalyst and reaction conditions can influence the conversion, selectivity, and yield of OCM and other coupling reactions.

One aspect of the process of the present invention involves the preparation of a catalyst for OCM. A catalyst of the present invention generally includes a substrate, one or more metal promoters and oxygen. The catalyst can vary in terms of its activity, useful run life, and others characteristics. This variation can influence the selection of the substrate and the combination of metal promoters supported by the substrate.

According to an embodiment, the catalyst of the present invention can include a substrate that ranges from 40 to 90 wt % of the catalyst, the substrate made of one or more of the elements of Set A consisting of: the Lanthanoid group (La, Ce, Pr, Nd, Sm, Eu, Gd, Tb, Dy, Ho, Er, Tb, Yb, Lu), Mg, Ca, and the elements of Group 4 of the periodic table (Ti, Zr, and Hf). The substrate supports a first promoter that ranges from 0.01 to 40 wt % of the catalyst chosen from one or more of the elements of Set B consisting of: Li, Na, K, Rb, Cs, and the elements of Group 3 (including La and Ac) and Groups 5-15 of the periodic table. The substrate further supports a second promoter that ranges from 0.01 to 40 wt % of the catalyst chosen from one or more of the elements of Set C consisting of: Li, Na, K, Rb, Cs, Ca, Sr, and Ba. If an element from Group 1 of the periodic table (Li, Na, K, Rb, Cs) is used as a catalytic element from Set B it cannot be used as a catalytic element from Set C. The catalyst further includes Set D, which consists of oxygen, in a range of 10 to 45 wt %. All percentages are for the catalyst after calcination.

The catalyst contains at least one element from each of the Sets A, B, C, and D in the ranges given above. At least 90 wt % of the catalyst is made of the elements of Sets A, B, C and oxygen in the final catalyst composition after a calcination procedure. Optionally at least 95 wt % of the catalyst is made of the elements of Sets A, B, C and D in the final catalyst after a calcination procedure. Residual anions may be present in the final catalyst, e.g. nitrate, halide, sulfate and acetate. The catalyst can vary in terms of its activity, its basicity, its lifetime, and other characteristics. This variation can be influenced by the selection of the elements chosen from Sets A, B, C and D and their respective content in the catalyst.

The various elements that make up the catalyst can be derived from any suitable source, such as in their elemental form, or in compounds or coordination complexes of an organic or inorganic nature, such as carbonates, oxides, hydroxides, nitrates, acetates, chlorides, phosphates, sulfides and sulfonates. The elements and/or compounds can be prepared by any suitable method, known in the art, for the preparation of such materials.

The term "substrate" as used herein is not meant to indicate that this component is necessarily inactive, while the other metals and/or promoters are the active species. On the contrary, the substrate can be an active part of the catalyst. The term "substrate" would merely imply that the substrate makes up a significant quantity, generally 40% or more by weight, of the entire catalyst. The promoters individually can range from 0.01% to 40% by weight of the catalyst, optionally from 0.01% to 10%. If more than one promoters are combined, they together generally can range from 0.01% up to 50% by weight of the catalyst. The elements of the catalyst composition can be provided from any suitable source, such as in its elemental form, as a salt, as a coordination compound, etc.

The addition of a support material to improve the catalyst physical properties is possible within the present invention. Binder material, extrusion aids or other additives can be added to the catalyst composition or the final catalyst composition can be added to a structured material that provides a support structure. For example, the final catalyst composition can be supported by a structured material comprising an alumina or aluminate framework. The content of such a binder material, extrusion aids, structured material, or other additives, and their respective calcination products, will not be taken into consideration within the stated percentage ranges of Sets A-D stated herein. As an additional example a binder material, which can contain elements that are contained within Sets A-D, can be added to the catalyst composition. Upon calcination these elements can be altered, such as through oxidation which would increase the relative content of oxygen within the final catalyst structure. The binder material elements and the calcination products are not taken into consideration within the stated percentage ranges of Sets A-D stated herein. The combination of the catalyst of the present invention combined with additional elements such as a binder, extrusion aid, structured material, or other additives, and their respective calcination products, are included within the scope of the invention.

In one aspect, the invention is a method for the preparation of an oxidative catalyst for OCM, or another oxidative coupling reaction. In one embodiment, the catalyst can be prepared by combining a substrate chosen from at least one element from Set A with at least one promoter element chosen from Set B, at least one promoter element chosen from Set C, and oxygen from Set D. The present invention is not limited by the method of catalyst preparation, and all suitable methods should be considered to fall within the scope herein. Particularly effective techniques are those utilized for the preparation of solid catalysts. Conventional methods include coprecipitation from an aqueous, an organic or a combination solution-dispersion, impregnation, dry mixing, wet mixing or the like, alone or in various combinations. In general, any method can be used which provides compositions of matter containing the prescribed components in effective amounts. According to an embodiment the substrate is charged with promoter via an incipient wetness impregnation. Other impregnation techniques such as by soaking, pore volume impregnation, or percolation can optionally be used. Alternate methods such as ion exchange, wash coat, precipitation, and gel formation can also be used. Various methods and procedures for catalyst preparation are listed in the technical report Manual of Methods and Procedures for Catalyst Characterization by J. Haber, J. H. Block and B. Dolmon, published in the International Union of Pure and Applied Chemistry, Volume 67, Nos 8/9, pp. 1257-1306, 1995, incorporated herein in its entirety.

In an embodiment, the substrate can be a metal oxide of one or more elements of Set A. One example of an oxide substrate useful for the present invention is magnesium oxide, MgO. The oxide substrate can be either obtained commercially or produced in the lab. For instance, a metal oxide can be made by thermal decomposition of its corresponding salt at elevated temperatures up to 750° C. The choice of precursor salt from which the oxide substrate is produced can have some effect on the performance of the eventual catalyst.

When slurries, precipitates or the like are prepared, they will generally be dried, usually at a temperature sufficient to volatilize the water or other carrier, such as about 100° C. to about 250° C. In all cases, irrespective of how the components are combined and irrespective of the source of the components, the dried composition is generally calcined in the presence of a free oxygen-containing gas, usually at temperatures between about 300° C. and about 900° C. for a period of time such as from 1 to 24 hours. The calcination can be in a reducing or inert atmosphere or an oxygen-containing atmosphere.

Depending on the catalyst, a pretreatment of the catalyst may, or may not, be necessary. In one embodiment the invention involves the pretreatment of an oxidative catalyst for OCM, the oxidative methylation of toluene (OMT), or another oxidative coupling reaction. The prepared catalyst can be ground, pressed and sieved and loaded into a reactor. The reactor can be any type known in the art to make catalyst particles, such as a fixed bed, fluidized bed, or swing bed reactor. The reactor set-up can optionally include a recycle stream. Optionally an inert material, such as quartz chips, can be used to support the catalyst bed and to place the catalyst within the bed. For the pretreatment, the reactor can be heated to elevated temperatures, such as 800° C. to 900° C. with an air flow, such as 100 mL/min, and held at these conditions for a length of time, such as 1 to 3 hours. Then, the reactor can be cooled down to a temperature of around the operating temperature of the reactor, for example 500° C. to 650° C., or optionally down to atmospheric or other desired temperature. The reactor can be kept under an inert purge, such as under helium.

Another aspect of the process of the present invention is a set of reaction conditions used in OCM and other coupling reactions. Several parameters including feed composition, molar ratio of hydrocarbon reactant to oxygen, temperature, pressure, time on stream, preparation method, particle size, porosity, surface area, contact time and others can influence the outcome of the reaction. For almost every reaction condition, there can be a range of values best suited to oxidative coupling. Measures are generally taken to increase conversion and selectivity.

For the oxidative coupling of methane, contents of the feed can include methane and an oxygen source. Oxygen is a required component of the feed for oxidative coupling. Methane can be obtained from natural gas, or from organic sources, such as the decomposition of waste through fermentation. Whatever the source, methane used in OMT should not contain contaminants that might significantly interfere or give a detrimental effect on the oxidative coupling reaction. The oxygen source can be any source suitable for providing oxygen to the reaction zone such as pure oxygen, oxygen-enriched air, or air. The gas containing oxygen should not contain any contaminants that might significantly interfere with the oxidative coupling reaction. Alternate sources of oxygen may also be used, such as nitrobenzene, nitrous oxide or other oxygen containing compounds.

Although contaminants that might significantly interfere with the oxidative coupling reaction should be avoided, the addition of trace quantities of a reaction modulator may be useful. Reaction modulators can be used for the control or alteration of conversion, selectivity, or activity of a particular catalyst or in response to certain reaction conditions. Non-limiting examples of possible reaction modulators include chlorine, ethylene and carbon monoxide.

Inert diluents such as helium and nitrogen may be included in the feed to adjust the gas partial pressures. Optionally, $CO_2$ or water (steam) can be included in the feed stream as these components may have beneficial properties, such as in the prevention of coke deposits. The pressure for oxidative coupling reactions can generally range from 1 psia to 200 psia or more. The reaction pressure is not a limiting factor regarding the present invention and any suitable condition is considered to be within the scope of the invention.

The temperature for oxidative coupling reactions can generally range from 500° C. to 800° C., optionally from 600° C. to 750° C. The reaction temperature is not a limiting factor regarding the present invention and any suitable condition is considered to be within the scope of the invention. The methane to oxygen molar ratio can range from 1:1 to 100:1, optionally from 4:1 to 80:1.

Any suitable space velocity can be considered to be within the scope of the invention. As used herein the space velocity shall be defined as: space velocity=[feed flow as vapor ($cm^3$/h)]/[catalyst weight (g)]. The space velocity can generally range from 15,000 $cm^3$ $g^{-1}$ $h^{-1}$ to 100,000 $cm^3$ $g^{-1}$ $h^{-1}$, optionally from 20,000 $cm^3$ $g^{-1}$ $h^{-1}$ to 85,000 $cm^3$ $g^{-1}$ $h^{-1}$. This range is an indication of possible space velocities, such as for a fixed bed reactor. Of course altering the catalyst composition, the amount of inert material, etc can alter the space velocity outside of this range. Also a change in the reactor from a fixed bed to an alternate design, such as a fluidized bed can also dramatically change the relative space velocity and can be outside of the stated range above. The space velocity ranges given are not limiting on the present invention and any suitable condition is considered to be within the scope of the invention.

The following equations, Equations 1-2, are reactions that can take place in the reactor over the OCM catalyst. The equations are shown along with their change in enthalpy, or heat of reaction. As Equations 1-2 demonstrates the reactions that occur during OCM are exothermic.

$$2CH_4 + 0.5O_2 \longrightarrow C_2H_6 + H_2O; \Delta H = -174.2 \text{ kJ/mole} \quad \text{Equation 1}$$

$$C_2H_6 + 0.5O_2 \longrightarrow C_2H_4 + H_2O; \Delta H = -103.9 \text{ kJ/mole} \quad \text{Equation 2}$$

The following examples are intended to give a better understanding of certain aspects and embodiments of the present invention, and are not intended to limit the scope of the invention in any way.

Comparative Example A

An oxidative catalyst was prepared comprising a MgO substrate that was promoted with Ba. The Ba/MgO catalyst was used in the oxidative coupling of methane and the oxidative methylation of toluene. The catalyst included 5% Ba by weight and was prepared from barium nitrate (6.53 g) (Sigma Aldrich, 98.0%) and MgO (23.46 g) (Fisher, 99%) by incipient wetness impregnation methodology in aqueous solution. The mixture was dried at 120° C. for 3 h and then calcined at 850° C. in air for 1 h. The catalyst was ground, pressed and sieved to 20-40 mesh size (420-841 μm) and 0.577 g of catalyst was loaded into a quartz reactor using quartz wool plugs and quartz chips to hold the catalyst bed in place. For catalyst pretreatment, the reactor was heated to 850° C. under 100 ml/min of air and held for 2 hours. The reactor was then cooled down to 600° C. under helium to prepare for the OCM experiments.

Two OCM trials were conducted. In one trial, the reactor temperature was 600° C.; in the other trial, the reactor temperature was 650° C. All reaction conditions other than temperature were held constant during the two trials. The oxygen source was air. The methane to oxygen molar ratio was 5:1. The total flow of gasses was 500 cm$^3$/min (250 cm$^3$/min air and 250 cm$^3$/min methane), space velocity of 51,993 cm$^3$ g$^{-1}$ h$^{-1}$. The following table shows the results of the two trials. C$_2$ selectivity as used herein is the cumulative selectivity of acetylene, ethane, and ethylene.

TABLE 1

Results for OCM over Ba/MgO catalyst

|  | Reaction Temperature | |
| --- | --- | --- |
|  | 600° C. | 650° C. |
| Methane Conversion (mol %) | 0.3 | 14.3 |
| C$_2$s selectivity (%) | 54.3 | 68.2 |
| Acetylene Selectivity (%) | 0 | 5.3 |
| Ethane Selectivity (%) | 54.3 | 31.6 |
| Ethylene Selectivity (%) | 0 | 31.4 |
| CO$_2$ Selectivity (%) | 31.4 | 28.7 |
| CO Selectivity (%) | 14.3 | 3.0 |

As shown in Table 1, there was very little methane activation at 600° C. and no production of ethylene. At 650° C., methane conversion was higher, at 14.3%, and the ethylene selectivity was 31.4%.

Example B

An oxidative catalyst was prepared comprising an oxide substrate, MgO, that was promoted with Sr and La. The Sr/La/MgO catalyst was used in the oxidative coupling of methane. The catalyst included 5% Sr by weight from strontium nitrate (3.62 g) and 5% La by weight from lanthanum oxide (3.51 g) and was prepared from Sr(NO$_3$)$_2$ salt, La$_2$O$_3$ (Sigma Aldrich, 98.0%) and MgO (22.85 g) (Fisher, 99%) by incipient wetness impregnation methodology in aqueous solution. The mixture was dried at 120° C. for 3 hours and then calcined at 850° C. in air for 1 hour. The catalyst was ground and sieved to 20-40 mesh size and 0.855 g of catalyst was loaded in a quartz reactor using quartz wool plugs and quartz chips to hold the catalyst bed in place. As a form of catalyst pretreatment, the reactor was heated to 850° C. under 100 ml/min of air and held for 2 hours. The reactor was then cooled down to 600° C. under helium to prepare for the OCM experiments.

Five OCM trials were conducted using the Sr/La/MgO catalyst. The five trials correspond to five temperatures between 500° C. and 700° C. For all five trials, the oxygen source was air, the total flow of gasses was 500 cm$^3$/min (250 cm$^3$/min methane, 250 cm$^3$/min air), the methane to oxygen molar ratio was 5:1, and the space velocity was 35,088 cm$^3$ g$^{-1}$ h$^{-1}$. After the first 25 minutes, the corresponding gas samples were analyzed for product distribution and selectivity. Table 2 shows the results of the five OCM trials.

TABLE 2

Results for OCM over Sr/La/MgO catalyst

|  | Temperature | | | | |
| --- | --- | --- | --- | --- | --- |
|  | 500° C. | 550° C. | 600° C. | 650° C. | 700° C. |
| Methane Conversion (wt %) | 19.4 | 23.1 | 34.9 | 36.1 | 35.8 |
| C$_2$ selectivity (%) | 3.8 | 3.2 | 29.9 | 33.4 | 33.8 |

TABLE 2-continued

Results for OCM over Sr/La/MgO catalyst

|  | Temperature | | | | |
| --- | --- | --- | --- | --- | --- |
|  | 500° C. | 550° C. | 600° C. | 650° C. | 700° C. |
| Acetylene Selectivity (%) | 0 | 0 | 0.9 | 0.7 | 0.7 |
| Ethane Selectivity (%) | 3.8 | 3.2 | 14.2 | 16.1 | 15.6 |
| Ethylene Selectivity (%) | 0 | 0 | 14.8 | 16.6 | 17.5 |
| CO$_2$ Selectivity (%) | 0 | 1.5 | 5.7 | 3.9 | 3.0 |
| CO Selectivity (%) | 44.5 | 40.4 | 3.0 | 3.5 | 3.5 |

The selectivity of C$_2$ products (acetylene, ethane, and ethylene) was limited and the partial oxidation product, CO, took up a large portion of the products below 600° C. At 600° C. and above, methane conversion was higher, C$_2$ products had a higher selectivity while the selectivity for CO was lower.

FIG. 1 is a graphical representation of the data shown in Table 7. At a temperature between 550° C. and 600° C., methane conversion and C$_2$ selectivity increased suddenly, while CO selectivity drops dramatically.

Example C

An oxidative catalyst was prepared comprising a MgO substrate that was promoted with Na, Cs, and Re. The Na/Cs/Re/MgO catalyst was used in the oxidative coupling of methane. The catalyst included 5% Na by weight (3.811 g) of sodium chloride, 5% Cs by weight (2.199 g) of cesium nitrate, and 0.01% Re by weight (0.5856 g) of rhenium chloride and MgO (23.4033 g) (Fisher, 99%) by incipient wetness impregnation methodology in aqueous solution. The mixture was dried at 120° C. for 3 h and then calcined at 850° C. in air for 1 h. The catalyst was ground and sieved to 20-40 mesh size (420-841 µm) and 0.597 g of catalyst was loaded into a quartz reactor using quartz wool plugs and quartz chips to hold the catalyst bed in place. For catalyst pretreatment, the reactor was heated to 850° C. under 100 ml/min of air and held for 2 hours. The reactor was then cooled down to 600° C. under helium to prepare for the OCM and OMT experiments.

Four OCM trials were conducted, at reaction temperatures between 600° C. and 750° C. In all trials, the oxygen source was air, the total flow of gasses was 500 cm$^3$/min (250 cm$^3$/min air, 250 cm$^3$/min methane), the methane to oxygen molar ratio was 5:1, and the space velocity was 50,251 cm$^3$ g$^{-1}$ h$^{-1}$. Product samples were taken after the twenty-five minutes of run time and analyzed for product distribution. The results of the trials are shown in the table below.

TABLE 3

Results for OCM over Na/Cs/Re/MgO catalyst

|  | Temperature | | | |
| --- | --- | --- | --- | --- |
|  | 600° C. | 650° C. | 700° C. | 750° C. |
| Methane Conversion (wt %) | 0.2 | 0.4 | 1.0 | 4.8 |
| C$_2$ Selectivity (wt %) | 0.0 | 0.0 | 0.0 | 4.8 |
| Acetylene Selectivity (wt %) | 0.0 | 0.0 | 0.0 | 0.0 |
| Ethane Selectivity (wt %) | 0.0 | 0.0 | 0.0 | 3.8 |
| Ethylene Selectivity (wt %) | 0.0 | 0.0 | 0.0 | 1.0 |
| CO$_2$ Selectivity (wt %) | 0.0 | 17.6 | 14.6 | 9.8 |
| CO Selectivity (wt %) | 0.0 | 0.0 | 0.0 | 10.8 |

Figures are used herein to illustrate data, which are shown as data points on a graph. Lines connecting the data points are used to guide the eye and assist in illustrating general trends of the data. The lines are not intended as a predictor of where additional data points would necessarily fall, if they were available.

The term "$C_2$ selectivity" as used herein is the cumulative selectivity of acetylene, ethane, and ethylene.

The abbreviation of "OCM" as used herein refers to oxidative coupling of methane. For instance, methane can couple with methane to form higher hydrocarbons such as ethane or ethylene.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

As used herein the space velocity shall be defined as: space velocity=[feed flow as vapor ($cm^3$/h)]/[catalyst weight (g)].

The above examples demonstrate possible embodiments of the present invention. Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What is claimed is:

1. A method for the oxidative coupling of methane comprising:
    placing a selected oxidative catalyst within a reactor, the catalyst comprising a substrate consisting essentially of a metal oxide of one or more elements selected from group (A), a promoter from group (C), and (D);
    wherein:
    (A) is at least one element selected from the group consisting of the Lanthanoid group, Mg, and Ca;
    (C) is at least one element selected from the group consisting of the elements Ca, Sr, and Ba, and wherein the substrate supports the promoter; and
    (D) oxygen;
    forming an oxidative catalyst containing the selected elements;
    pretreating the catalyst formed thereby prior to the oxidative coupling, wherein the pretreating step includes heating the reactor containing the catalyst to a pretreatment temperature of between 800° C. and 900° C. and holding the reactor containing the catalyst at the pretreatment temperature for between 1 and 3 hours;
    cooling the reactor down from the pretreatment temperature to an oxidative coupling reaction temperature ranging from 500° C. to 750° C.;
    providing a hydrocarbon feedstream comprising methane;
    feeding the hydrocarbon feedstream and a gas flow comprised of oxygen to the reactor containing the oxidative catalyst;
    carrying out an oxidative coupling of methane within the reactor at the oxidative coupling reaction temperature to thereby form higher hydrocarbons comprised of ethane, ethylene, and combinations thereof over the oxidative catalyst according to reaction conditions; and
    recovering a product stream of higher hydrocarbons from the reactor.

2. The method of claim 1, wherein the at least one element selected in (A) ranges from 40 to 90 wt% of the catalyst.

3. The method of claim 1, wherein the catalyst comprises a Ba/MgO catalyst.

4. The method of claim 3, wherein the at least one element selected in (C) ranges from 0.01 to 40 wt% of the catalyst.

5. The method of claim 3, wherein the oxygen in (D) ranges from 10 to 45 wt% of the catalyst.

6. The method of claim 3, wherein the catalyst is calcined after the elements are combined by an incipient wetness impregnation in an aqueous solution, and wherein the calcination of the catalyst comprises heating to above 750° C. to 900° C. with an air flow.

7. The method of claim 3, wherein atmospheric air is a source of the gas flow comprised of oxygen.

8. The method of claim 7, wherein a composition of the product hydrocarbons can be adjusted by adjusting the temperature of the reaction.

9. The method of claim 3, wherein the oxidative coupling of methane occurs within a molar ratio of methane to oxygen of from 1:1 to 100:1.

10. The method of claim 3, wherein a composition of the product hydrocarbons can be adjusted by adjusting a space velocity of the reaction.

11. The method of claim 1, wherein the oxidative catalyst is further comprised of a promoter from group (B);
    wherein (B) is at least one element selected from the group consisting of the elements of Group 3 of the periodic table; and
    wherein the substrate supports the promoter.

12. The method of claim 11, wherein the catalyst comprises a Sr/La/MgO catalyst.

13. The method of claim 12, wherein the oxidative coupling of methane occurs within the reactor at a molar ratio of methane to oxygen of from 1:1 to 100:1.

14. The method of claim 12, wherein the elements of the catalyst are combined by an incipient wetness impregnation in an aqueous solution.

15. The method of claim 12, wherein a composition of the product hydrocarbons can be adjusted by adjusting the temperature of the reaction.

16. The method of claim 12, wherein a composition of the product hydrocarbons can be adjusted by adjusting a space velocity of the reaction.

17. The method of claim 12, wherein the at least one element selected in (A) ranges from 40 to 90 wt% of the catalyst;
    wherein the at least one element selected in (C) ranges from 0.01 to 40 wt% of the catalyst;
    wherein the oxygen in (D) ranges from 10 to 45 wt% of the catalyst; and
    wherein atmospheric air is a source of the gas flow comprised of oxygen.

18. The method of claim 11, wherein the catalyst comprises an Sr/La/MgO catalyst, and wherein the oxidative coupling reaction temperature ranges from 600° C. to 750° C.

19. The method of claim 1, wherein the at least one element selected in (A) includes Ce.

20. The method of claim 1, wherein the oxidative coupling reaction temperature ranges from 600° C. to 750° C. and the CO selectivity is from 0.0 to 10.8.

21. The method of claim 1, wherein the oxidative coupling reaction temperature ranges from 600° C. to 750° C. and the methane conversion is from 4.8 to 36.1.

22. The method of claim 1, wherein the oxidative coupling reaction temperature ranges from 600° C. to 750° C. and the $C_2$ selectivity is from 4.8 to 33.8.

23. A method for the oxidative coupling of methane comprising:
   placing an oxidative catalyst within a reactor, the catalyst consisting essentially of a substrate of a metal oxide selected from one or more elements of group (A), an optional promoter from group (B), a promoter from group (C), and (D);
   wherein:
   (A) is at least one element selected from the group consisting of the Lanthanoid group and Mg, and Ca, the elements from (A) ranging from 40 to 90 wt% of the catalyst;
   (B) is an optional promoter selected from the group consisting of the elements of Group 3;
   (C) is at least one element selected from the group consisting of the elements Ca, Sr, and Ba, the elements from (C) ranging from 0.01 to 40 wt% of the catalyst;
   (D) oxygen ranging from 10 to 45 wt% of the catalyst;
   forming an oxidative catalyst containing the selected elements, and wherein the catalyst is calcined at 800° C. to 900° C. after the catalyst formation;
   pretreating the catalyst formed thereby prior to the oxidative coupling, wherein the pretreating step includes heating the reactor containing the catalyst to a pretreatment temperature of between 800° C. and 900° C. and holding the reactor containing the catalyst at the pretreatment temperature for between 1 and 3 hours;
   cooling the reactor down from the pretreatment temperature to an oxidative coupling reaction temperature ranging from 500° C. to 800° C.;
   providing a hydrocarbon feedstream comprising methane;
   feeding the hydrocarbon feedstream and a gas flow comprised of oxygen to the reactor Having the calcined oxidative catalyst therein;
   carrying out an oxidative coupling of methane within the reactor at the oxidative coupling reaction temperature to thereby form higher hydrocarbons comprised of ethane, ethylene, and combinations thereof over the oxidative catalyst according to reaction conditions; and
   recovering product hydrocarbons comprising ethane and ethylene from the reactor.

* * * * *